US012558544B2

(12) United States Patent
Tourrel et al.

(10) Patent No.: US 12,558,544 B2
(45) Date of Patent: Feb. 24, 2026

(54) COCHLEAR IMPLANT WITH MULTI-LAYER ELECTRODE

(71) Applicants:Cochlear Limited, Macquarie University (AU); ESPCI Paris, Paris (FR)

(72) Inventors: Guillaume Tourrel, Vallauris (FR); Léa Milenkovic, Paris (FR); Yvette Tran, Paris (FR); Dominique Hourdet, Paris (FR); Zuxiang Xu, Paris (FR)

(73) Assignees: Cochlear Limited, Macquarie University (AU); ESPCI Paris, Paris (FR)

( * ) Notice: Subject to any disclaimer, the term of this patent is extended or adjusted under 35 U.S.C. 154(b) by 585 days.

(21) Appl. No.: 17/969,147

(22) Filed: Oct. 19, 2022

(65) Prior Publication Data

US 2023/0120291 A1 Apr. 20, 2023

(30) Foreign Application Priority Data

Oct. 20, 2021 (EP) .................................... 21203704

(51) Int. Cl.
*A61N 1/36* (2006.01)
*A61N 1/05* (2006.01)
*H04R 25/00* (2006.01)

(52) U.S. Cl.
CPC ....... *A61N 1/36038* (2017.08); *A61N 1/0541* (2013.01); *A61N 1/36185* (2013.01); *H04R 25/606* (2013.01)

(58) Field of Classification Search
CPC .............. A61N 1/36038; A61N 1/0541; A61L 2300/414; A61L 27/34; A61L 27/3834
See application file for complete search history.

(56) References Cited

U.S. PATENT DOCUMENTS

| 4,207,441 | A | 6/1980 | Ricard et al. |
| 4,532,930 | A | 8/1985 | Crosby et al. |

(Continued)

OTHER PUBLICATIONS

Boston's Children's Hospital, "Gene therapy restores hearing in deaf mice . . . down to a whisper", Mar. 27, 2017, Harvard Stem Cell Institute (Year: 2017).*

(Continued)

*Primary Examiner* — Catherine M Voorhees
(74) *Attorney, Agent, or Firm* — Edell, Shapiro & Finnan, LLC

(57) ABSTRACT

A cochlear hearing aid system for providing electrical stimulation to auditory nerve fibers of a cochlea of a recipient of the cochlear hearing aid system is disclosed. The cochlear hearing aid system comprises a microphone configured to receive an acoustical signal and provide an audio signal based on the acoustical signal; a signal processor unit configured to receive the audio signal and process the audio signal; an electrode lead including a plurality of electrodes configured to stimulate the auditory nerve fibers based on the processed audio signal, wherein the electrode lead comprises: an electrode carrier maintaining the electrode contacts and wires, wherein the electrode carrier is made of silicone and is loaded by dexamethasone; a first layer (or sub-layers) of gelatin which is coated and chemically cross-linked selectively on a silicone outer surface of the electrode lead, wherein dexamethasone sodium phosphate is embedded in the first layer (or sub-layers); and a second layer of gelatin which is coated and physically cross-linked onto the first layer.

13 Claims, 14 Drawing Sheets

(56)                    References Cited

U.S. PATENT DOCUMENTS

2004/0225336 A1* 11/2004 Milojevic ............ A61N 1/0541
                                                  607/57
2009/0062896 A1*  3/2009 Overstreet ........... A61K 9/0046
                                                  607/137
2013/0079749 A1   3/2013 Overstreet et al.
2017/0326254 A1* 11/2017 Chen ................... A61K 9/0046
2019/0381309 A1  12/2019 Tritthart

OTHER PUBLICATIONS

Qnouch et al., "Dexamethasone-loaded cochlear implants: How to provide a desired burst release", Jul. 2, 2021, International Journal of Pharmaceutics: X, Elsevier, pp. 1-10 (Year: 2021).*
Extended European Search Report, issued in Priority Application No. 21203704.8, dated Apr. 7, 2022.
Plontke et al., "Intracochlear drug delivery in combination with cochlear implants: Current aspects", HNO, 2017, 65 (Suppl 1), pp. S19-S28.

* cited by examiner

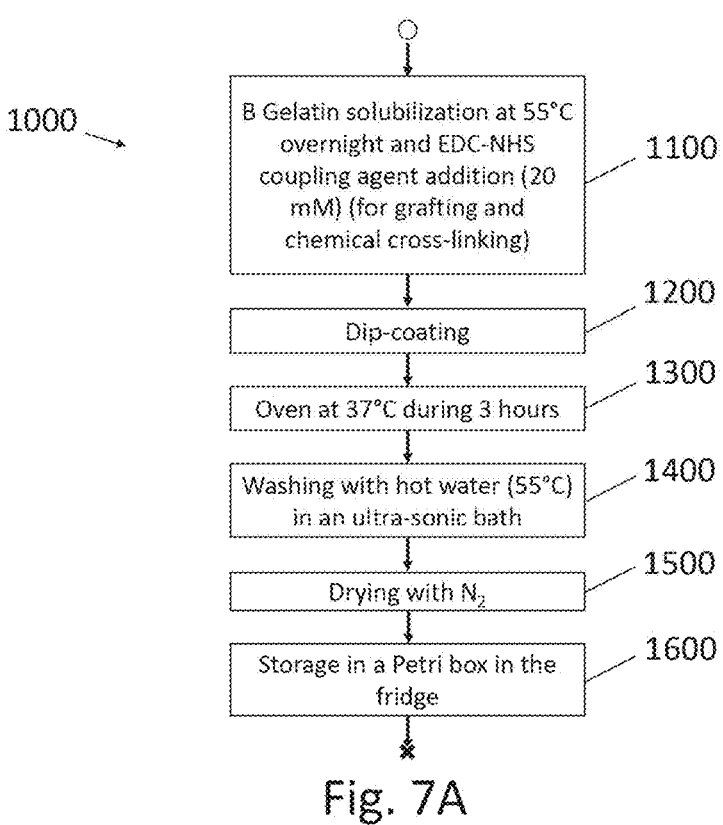
1000
B Gelatin solubilization at 55°C overnight and EDC-NHS coupling agent addition (20 mM) (for grafting and chemical cross-linking) — 1100
Dip-coating — 1200
Oven at 37°C during 3 hours — 1300
Washing with hot water (55°C) in an ultra-sonic bath — 1400
Drying with N₂ — 1500
Storage in a Petri box in the fridge — 1600
Fig. 7A
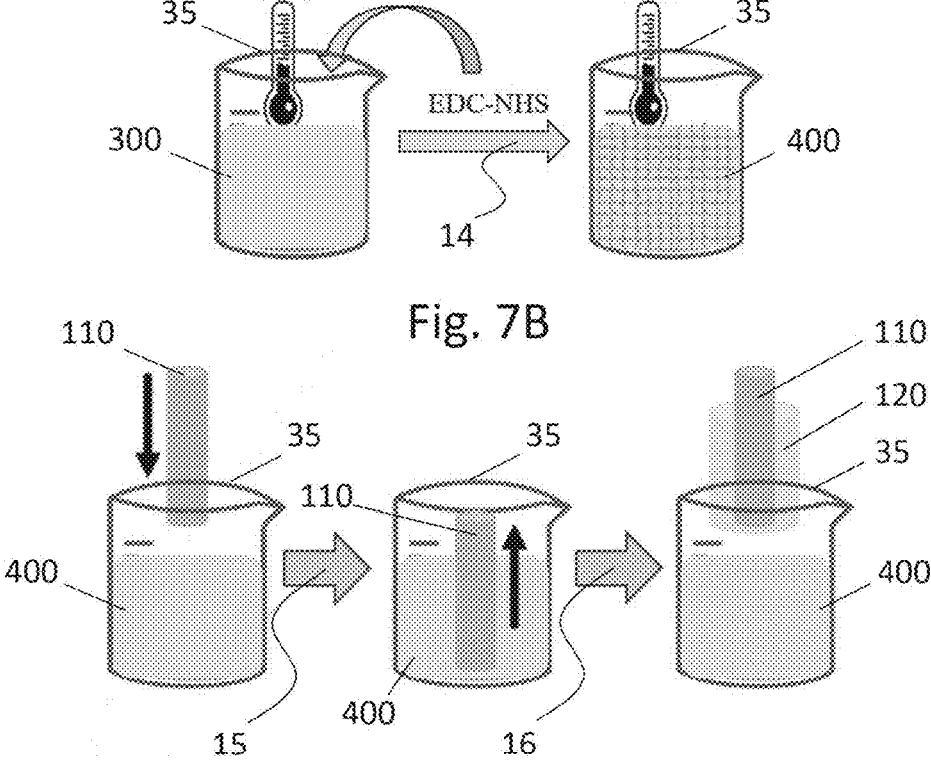
Fig. 7B
Fig. 7C

COCHLEAR IMPLANT WITH MULTI-LAYER ELECTRODE

FIELD

The present disclosure relates to a cochlear hearing aid system and to a method for delivering a substance into a cochlea of a recipient of a cochlear hearing aid system.

BACKGROUND

A cochlear implant allows a person, e.g. a person suffering from sensorineural hearing loss, to perceive acoustic stimuli by directly stimulating the person's auditory nerves with electric signals. To this end, cochlear implants typically comprise an electrode array that is embedded in the person's cochlea. However, inserting the electrode array of the cochlear implant into the person's cochlea may cause a cochlear trauma due to mechanical insertion forces. While robot assisted surgery could possibly help to mitigate the cochlear trauma by providing a slower and more regular insertion of the electrode array into the cochlea, most electrode insertions are still performed manually nowadays. On the other hand, surgeons have tried to mitigate cochlear trauma by applying sodium hyaluronate on top of the round window (an opening of the middle ear into the inner ear) before inserting the electrode array therethrough. However, it is unclear if the electrode array actually carries the sodium hyaluronate through the round window into the cochlear and if there is an effect on the friction during insertion. In particular, the sodium hyaluronate might be wiped from the electrode array by the round window membrane during insertion.

Further, in order to avoid inflammation of tissue as a result of the cochlear trauma, it is desirable to deliver anti-inflammatory drugs to the inner ear. While it is possible to load the silicone component enclosing the electrode array with anti-inflammatory drugs, the amount of drug released from the drug-loaded silicone component is comparatively low during the first days after implantation. As a result, the desired prompt anti-inflammatory effect after inserting the electrode array may not be achieved. On the other hand, it is also possible to directly inject the anti-inflammatory drugs through the tympanic membrane into the middle ear cavity. However, in this case, it is unclear to which extent the anti-inflammatory drugs will diffuse from the middle ear cavity into the inner ear, in particular since the injected drug may simply drain into the Eustache trump.

SUMMARY

It is thus an object to provide a cochlear hearing aid system allowing for a reduction of cochlear trauma caused by insertion of the cochlear hearing aid system into a recipient's cochlea and providing drug release in the cochlea with enhanced control, in particular with regard to a temporal drug release profile. It is a further object to provide a method for delivering a substance into a cochlea of a recipient of a cochlear hearing aid system offering the aforementioned advantages.

According to a first aspect, a cochlear hearing aid system for providing electrical stimulation to auditory nerve fibers of a cochlea of a recipient of the cochlear hearing aid system is provided, the cochlear hearing aid system comprising: a microphone configured to receive an acoustical signal and provide an audio signal based on the acoustical signal; a signal processor unit configured to receive the audio signal and process the audio signal; an electrode lead including a plurality of electrodes configured to stimulate the auditory nerve fibers based on the processed audio signal, wherein the electrode lead comprises: an electrode carrier maintaining the electrode contacts and wires, wherein the electrode carrier is made of silicone and is loaded by dexamethasone; a first layer of gelatin which is coated and chemically cross-linked selectively on a silicone outer surface of the electrode lead, wherein dexamethasone sodium phosphate is embedded in the first layer; and a second layer of gelatin which is coated and physically cross-linked onto the first layer.

According to a second aspect, a method for delivering a substance into a cochlea of a recipient of a cochlear hearing aid system is provided, the method comprising: applying a first layer at least partially onto an outer surface of an electrode lead of the cochlear hearing aid system, wherein the first layer includes a gelatin substance; coating a second layer onto the first layer, wherein the second layer includes a gelatin substance; and inserting the electrode lead into the cochlea of the recipient.

It has been found that a combination of a first layer of gelatin which is coated and chemically cross-linked selectively on a silicone outer surface of the electrode lead and of a second layer of gelatin which is coated and physically cross-linked onto the first layer significantly enhances the lubricity of the electrode lead, thereby significantly reducing a maximum insertion and/or friction force acting on the recipient's cochlea during insertion of the electrode lead into the recipient's cochlea, e.g. by at least 30%. In this way, said first and second gelatin layers in combination allow to reduce cochlear trauma occurring when the electrode lead is inserted in the recipient's cochlea.

It has further been found that by embedding dexamethasone sodium phosphate (DSP), a glucocorticoid with anti-inflammatory effects (immune response decrease), in the first layer, and by loading the silicone electrode carrier by dexamethasone, an enhanced control of drug release in the cochlea is enabled. In particular, while the dexamethasone sodium phosphate embedded in the first layer enables a desired short-term drug release promptly after insertion of the electrode lead into the recipient's cochlea, the dexamethasone loaded onto the silicone electrode carrier enables a long-term drug release desired as well. Thereby, short-term may be understood as a time period of between 1 hour and 72 hours, in particular approximately 24 hours, after insertion of the electrode lead, and long-term may be understood as a time period of between 1 year and 5 years, in particular approximately 3 years, after insertion of the electrode lead. The combination of the first layer, in which dexamethasone sodium phosphate is embedded, and the silicone electrode carrier, onto which dexamethasone is loaded, allows to achieve the desired temporal drug release profile, i.e. a superposition of an increased, peak or burst short-term drug release after insertion of the electrode lead, e.g. over several hours, and a subsequent long-term drug release, e.g. over several years. Achieving the desired temporal drug release profile in turn allows to avoid inflammation of tissue as a result of the cochlear trauma.

A further advantage of the first and second layers, due to said layers consisting of a gelatin (substance), thus representing biopolymer coatings, is that said layers are biocompatible and biodegradable.

Exemplary embodiments of any aspect may have one or more of the properties described below.

In an exemplary embodiment, the plurality of electrodes included in the electrode lead represents an electrode array.

Thereby, an electrode array may be understood as an array, in particular a one-dimensional array, of electrodes spatially arranged along one (in the case of a one-dimensional array) or more dimensions. In other words, in an exemplary embodiment, the electrode lead comprises a one-dimensional array of electrodes arranged a longitudinal direction of the electrode lead. The electrodes included in the electrode lead advantageously allow to electrically stimulate the auditory nerve fibers of the recipient's cochlea, thereby allowing the recipient to perceive acoustic stimuli.

In an exemplary embodiment, the electrode lead has a length substantially corresponding to a length of an inner cavity of the cochlea. Thereby, substantially corresponding may be understood as differing not more than 50%, in particular not more than 20%, in particular not more than 10%. By adapting the length of the electrode lead to the inner-cavity length of the cochlea, the electrode lead advantageously fits into the inner cavity of the cochlea.

In an exemplary embodiment, stimulating the auditory nerve fibers comprises electrically stimulating the cochlear nerve of the recipient. Electrically stimulating the cochlear nerve may be understood as providing an electrical current to the cochlear nerve, wherein the electrical current imitates electrochemical impulses generated in a healthy inner ear from sound pressure patterns representative of acoustic signals. Electrically stimulating the auditory nerve fibers advantageously allows a person, e.g. a person suffering from sensorineural hearing loss, to perceive acoustic stimuli.

In an exemplary embodiment, the electrode lead comprises electrode contacts and electrode wires as respective parts of the plurality of electrodes included by the electrode lead. That the electrode carrier maintains the electrode contacts and wires may thus mean that the electrode carrier at least partially physically encloses the plurality of electrodes. In other words, in an exemplary embodiment, the electrode lead comprises an electrode carrier and a plurality of electrodes embedded in and/or enclosed by the electrode carrier, wherein each of the plurality of electrodes comprises at least one electrode contact and/or at least one electrode wire.

That the electrode carrier is made of silicone means, in an exemplary embodiment, that the electrode carrier consists of silicone. Using an electrode carrier made of or consisting of silicone is advantageous in that such an electrode carrier provides high flexibility while still having sufficient mechanical robustness and providing mechanical and/or chemical protection for the plurality of electrodes.

In an exemplary embodiment, the electrode carrier is loaded by dexamethasone at between 5 and 15% weight, in particular at between 8 and 12% weight, in particular at 10% weight. It has been found that the aforementioned amount of dexamethasone loaded onto the electrode carrier advantageously provides an amount of released drug desired in the long-term regime.

That the first layer is coated and chemically cross-linked selectively on a silicone outer surface of the electrode lead means, in an exemplary embodiment, that an outer surface of the electrode carrier is coated and chemically cross-linked selectively with the first layer. Thereby, in an exemplary embodiment, chemically cross-linking means linking polymer chains to each other by means of one or more covalent or ionic bonds. It has been found that, by coating and chemically cross-linking the first layer selectively on the silicone outer surface of the electrode lead, a particularly strong attachment of the first layer on the silicone outer surface and thus on the electrode lead is achieved due to covalent (or ionic) bonding, thereby avoiding a possible removal of the first layer from the electrode lead during insertion. It has further been found that coating and chemically cross-linking the first layer selectively on the silicone outer surface of the electrode lead also allows for an enhanced control of a thickness of the first layer.

That the dexamethasone sodium phosphate is embedded in the first layer means, in an exemplary embodiment, that the dexamethasone sodium phosphate has previously been absorbed, resorbed, soaked up and/or sucked up by the first layer, and/or that the first layer comprises, contains, includes and/or holds the dexamethasone sodium phosphate. Alternatively or in addition, in an exemplary embodiment, the dexamethasone sodium phosphate sticks and/or adheres to a surface of the first layer. As already described above, embedding dexamethasone sodium phosphate in the first layer advantageously allows to release an amount of drug desired in the short-term regime.

That the second layer is coated and physically cross-linked onto the first layer means, in an exemplary embodiment, that an outer surface of the first layer is coated and physically cross-linked with the second layer. Thereby, in an exemplary embodiment, physically cross-linking means linking polymer chains to each other by means of weak interactions. It has been found that, by coating and physically cross-linking the second layer onto the first layer, a particularly high lubricity of the electrode lead is achieved, thereby reducing insertion/friction force during insertion of the electrode lead which in turn minimizes a possible cochlear trauma.

In an exemplary embodiment, the substance delivered into the cochlea of the recipient is a drug, in particular dexamethasone and/or dexamethasone sodium phosphate.

In an exemplary embodiment, delivering the substance into the cochlea of the recipient of the cochlear hearing aid system comprises embedding the substance in at least one component of the electrode lead of the cochlear hearing aid system. Thereby, in an exemplary embodiment, the at least one component is suitable for releasing the substance when the at least one component is in contact with body liquid.

In an exemplary embodiment, the gelatin substance included by the first layer and/or the gelatin substance included by the second layer is gelatin. In an exemplary embodiment, the gelatin is a B(-type) gelatin.

In an exemplary embodiment, applying the first layer at least partially onto an outer surface of the electrode lead comprises coating and chemically cross-linking the first layer selectively on a silicone outer surface of the electrode lead.

In an exemplary embodiment, coating the second layer onto the first layer comprises coating and physically cross-linking the second layer onto the first layer.

In an exemplary embodiment, inserting the electrode lead into the cochlea of the recipient comprises sticking or sliding, in particular manually, the electrode lead into the cochlea.

In an exemplary embodiment, several layers of gelatin are coated and cross-linked in order to reach a thicker first layer. In other words, in an exemplary embodiment, the first layer consists of a plurality of sub-layers of gelatin. Thereby, in an exemplary embodiment, a first of the plurality of sub-layers is coated and chemically cross-linked selectively on a silicone outer surface of the electrode lead and at least one second of the plurality of sub-layers is coated and chemically cross-linked on an outer surface of a respective previous sub-layer. Yet put differently, in an exemplary embodiment, the first layer consists of two, three, four, or N sub-layers which are each respectively coated and chemically cross-linked on a respective outer surface of a respective previous sub-layer. Thereby, a respective thickness of a respective sub-layer of the plurality of sub-layers may either be equal or different among the plurality of sub-layers. Using several layers (or using a plurality of sub-layers) in order to reach a thicker first layer, advantageously allows to control a thickness of the first layer, in particular to achieve a thickness which cannot be achieved with a single layer. Since the first layer embeds dexamethasone sodium phosphate, controlling the thickness of the first layer in turn advantageously allows to control the amount of dexamethasone sodium phosphate induced into the recipient's cochlea, in this way enabling to control the short-term drug release of the electrode lead.

In an exemplary embodiment, several layers of gelatin are coated and chemically/covalently cross-linked in order to reach a thicker total layer. In other words, in an exemplary embodiment, the total layer consists of a plurality of sub-layers of gelatin. Thereby, in an exemplary embodiment, a first of the plurality of sub-layers is coated and chemically/covalently cross-linked onto the first layer and the last layer can be coated and physically cross-linked on a respective previous chemically cross-linked sub-layers. Yet put differently, in an exemplary embodiment, the total layer consists of two, three, four, or N sub-layers which are each respectively coated and chemically cross-linked on a respective previous sub-layer. Thereby, a respective thickness of a respective sub-layer of the plurality of sub-layers may either be equal or different among the plurality of sub-layers. Using several layers (or using a plurality of sub-layers) in order to reach a thicker total layer, advantageously allows to control a thickness of the second layer, in particular to achieve a thickness which cannot be achieved with a single layer. The last layer can be a physically cross-linked layer which provides a particularly high lubricity, controlling the thickness of the last layer in turn advantageously allows to control the amount of highly lubricant substance, thereby enabling to control (in particular enhance) the lubricity of the electrode lead. As already described above, a particularly high lubricity of the electrode lead reduces insertion/friction force during insertion of the electrode lead and thus minimizes possible cochlear traumas.

In an exemplary embodiment, the first layer has a thickness of between 200 nm and 5 μm and/or is composed of a single layer or multiple layers. As already described above, controlling the thickness of the first layer allows to control the amount of dexamethasone sodium phosphate induced into the recipient's cochlea, in this way enabling to control the short-term drug release of the electrode lead. It has been found that in particular a first layer having a thickness of between 200 nm and 5 μm induces a short-term drug release of a desired quantity.

In an exemplary embodiment, some layers include a release drug solution. In other words, in an exemplary embodiment, the first layer, at least one sub-layer of the first layer, the second layer, at least one sub-layer of the second layer and/or a further layer include a release drug solution. Thereby, in an exemplary embodiment, a release drug solution is a solution containing a predetermined concentration of a drug. In an exemplary embodiment, the drug is dexamethasone sodium phosphate. That a layer includes the release drug solution means, in an exemplary embodiment, that the release drug solution has previously been absorbed, resorbed, soaked up and/or sucked up by the layer, and/or that the layer comprises, contains, includes and/or holds the release drug solution. Alternatively or in addition, in an exemplary embodiment, the release drug solution sticks and/or adheres to a surface of the layer. With some layers including the release drug solution, it is advantageously possible to control the short-term drug release of the electrode lead by controlling the concentration of the drug, in particular dexamethasone sodium phosphate, in the release drug solution.

In an exemplary embodiment, the release drug solution used for electrode preparation includes Dexamethasone Sodium Phosphate having a concentration of between 0.1 mg/mL and 100 mg/mL (saturated solution). In other words, in an exemplary embodiment, 1 mL of the release drug solution contains between 0.1 mg and 100 mg Dexamethasone Sodium Phosphate. Thereby, a release drug solution having a concentration of 100 mg/mL is saturated. It has been found that in particular a release drug solution having a dexamethasone sodium phosphate concentration of between 0.1 mg/mL and 100 mg/mL, in particular of between 0.5 mg/mL and 5 mg/mL, in particular of approximately 1 mg/mL leads to a desired concentration of the dexamethasone sodium phosphate in the perilymph, thereby advantageously controlling the short-term drug release.

In an exemplary embodiment, a released Dexamethasone Sodium Phosphate concentration is between 0.1 and 175 μg in 70 μL of artificial perilymph. In other words, in an exemplary embodiment, 70 μL of artificial perilymph contain between 0.1 and 175 μg of released dexamethasone sodium phosphate. In an exemplary embodiment, a released Dexamethasone Sodium Phosphate concentration is approximately 3 μg in 70 μL of artificial perilymph. Thereby, artificial perilymph may be understood as an artificial liquid modelling characteristics of human perilymph. It has been found that a concentration of between 0.1 and 175 μg, in particular of approximately 3 μg, of released dexamethasone sodium phosphate in 70 μL of artificial perilymph enable the desired anti-inflammatory effect of the dexamethasone sodium phosphate when the electrode lead is inserted into a recipient's cochlea in real life.

In an exemplary embodiment, the drug is released in a chosen duration of between 10 minutes and 1 day, depending on the coating characteristics, in particular concentration, thickness and cross-linking. In other words, in an exemplary embodiment, the release drug solution concentration, the thickness of the first layer, and the extent of cross-linking between the first layer and the electrode lead are characteristics of the coating, in particular of the first layer, which influence a duration during which the drug is released from the first layer into the perilymph. That the drug is released in a chosen duration of between 10 minutes and 1 day advantageously allows for the desired short-term drug release.

In an exemplary embodiment of the method according to the second aspect, the method further comprises applying a release drug solution into or onto the first layer. Thereby, in an exemplary embodiment, applying the release drug solution into or onto the first layer means that the release drug solution is absorbed, resorbed, soaked up and/or sucked up by the first layer and/or that the first layer comprises, contains, includes and/or holds the release drug solution. By applying the release drug solution into or onto the first layer, it is advantageously possible to control the short-term drug release of the electrode lead by controlling the concentration of the drug in the release drug solution.

In an exemplary embodiment, the first layer includes both the gelatin substance and a coupling agent, in particular EDC-NHS. The coupling agent allows for grafting and chemically cross-linking the first layer onto the electrode lead which in turn enables a particularly strong attachment of the first layer on the silicone outer surface and thus on the electrode lead due to covalent bonding, thereby advantageously avoiding a possible removal of the first layer from the electrode lead during insertion.

In an exemplary embodiment, the substance is coupled to stem cells targeting hair cells or neurons. In an exemplary embodiment, the substance is coupled to Nerve Growth Factor (NGF). Coupling the substance to stem cells targeting hair cells or neurons and/or to NGF in particular allows for a more efficient effect mechanism of the substance.

In an exemplary embodiment, applying the first layer comprises: dip-coating the electrode lead into a liquid, the liquid comprising the gelatin substance or the gelatin substance and a coupling agent; heating the electrode lead at a temperature between 30° C. and 45° C.; cleaning the electrode lead with water having a temperature of between 45° C. and 65° C.; and drying the electrode lead and cooling the electrode lead at below 0° C.

Thereby, in an exemplary embodiment, dip-coating the electrode lead into a liquid comprises: immersion of the electrode lead in the liquid at a predetermined immersion speed and/or for a predetermined dwell time; and withdrawal of the electrode lead out of the liquid at a predetermined withdrawal speed. In an exemplary embodiment, the immersion speed amounts to approximately 10 mm/s, the dwell time is variable, and/or the withdrawal speed amounts to approximately 5 mm/s. The aforementioned parameters have been found to be particularly advantageous for achieving reproducible properties of the first layer, thus providing enhanced control over the thickness of the first layer.

Further, in an exemplary embodiment, heating the electrode lead comprises depositing the electrode lead in a heating device, e.g. an oven, for a predetermined heating duration. In an exemplary embodiment, the heating duration is between 1 hour and 5 hours, in particular approximately 3 hours, and/or the electrode lead is heated at a temperature of approximately 37° C. In an exemplary embodiment, cleaning the electrode lead with water comprises washing the electrode lead with water having a temperature of approximately 55° C. in an ultra-sonic bath. In an exemplary embodiment, the electrode lead is dried and/or cooled with nitrogen.

In an exemplary embodiment, the release drug solution is applied into the liquid. Thus, in an exemplary embodiment, the liquid comprises the release drug solution. Applying the release drug solution into the liquid allows to reduce the number of steps necessary for preparing the electrode lead. By applying the release drug solution into the liquid and by subsequently dip-coating the electrode lead into the liquid, the first layer applied to the electrode lead already comprises the drug such that the step of applying the release drug solution into or onto the first layer can advantageously be dispensed with.

In an exemplary embodiment, the release drug solution is applied into or onto the first layer by: dip-coating the electrode lead with the first layer into a liquid comprising the release drug solution for a period of between 12 hours and 48 hours or until the first layer has a swelling ratio of between 1.5 and 1.7; and drying the electrode lead.

In an exemplary embodiment, the swelling ratio is determined as being the relation between the dry thickness in air of the gelatin layer and the swollen thickness in liquid of the layer. In other words, in an exemplary embodiment, the swelling ratio is representative of the swelling of the gelatin layer due to immersion into the liquid. Determining the swelling ratio allows to control the amount of release drug solution included by the first layer, thereby allowing to advantageously control the short-term drug release.

Herein, the disclosure of any feature of the method according to the second aspect shall also be considered as a disclosure for a respective feature of the cochlear hearing aid system according to the first aspect. Likewise, the disclosure of any feature of the cochlear hearing aid system according to the first aspect shall also be considered as a disclosure for a respective feature of the method according to the second aspect.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIG. 7A schematically shows some sub-steps of the second step of gelatin coating a PDMS fiber;

FIG. 7B schematically illustrates some details of some sub-steps of the second step of gelatin coating a PDMS fiber;

FIG. 7C schematically illustrates some details of some sub-steps of the second step of gelatin coating a PDMS fiber;

DETAILED DESCRIPTION

Figure 1:
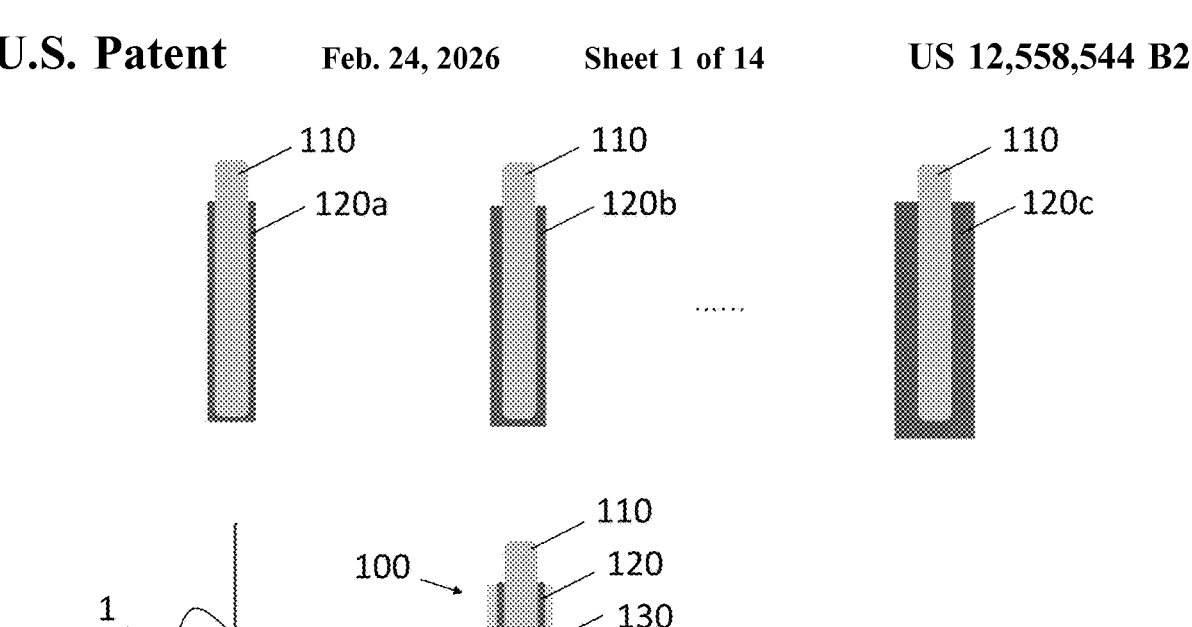
FIG. 1 schematically illustrates a multi-layer electrode lead according to an exemplary embodiment.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include micro-electronic-mechanical systems (MEMS), integrated circuits (e.g. application specific), microprocessors, microcontrollers, digital signal processors (DSPs), field programmable gate arrays (FPGAs), programmable logic devices (PLDs), gated logic, discrete hardware circuits, printed circuit boards (PCB) (e.g. flexible PCBs), and other suitable hardware configured to perform the various functionality described throughout this disclosure, e.g. sensors, e.g. for sensing and/or registering physical properties of the environment, the device, the user, etc. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device (or hearing instrument, hearing assistance device) may be or include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. 'Improving or augmenting the hearing capability of a user' may include compensating for an individual user's specific hearing loss. The "hearing device" may further refer to a device such as a hearable, an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of the middle ear of the user or electric signals transferred directly or indirectly to the cochlear nerve and/or to the auditory cortex of the user.

A "hearing system" refers to a system comprising one or two hearing devices, and a "binaural hearing system" or a bimodal hearing system refers to a system comprising two hearing devices where the devices are adapted to cooperatively provide audible signals to both of the user's ears either by acoustic stimulation only, acoustic and mechanical stimulation, mechanical stimulation only, acoustic and electrical stimulation, mechanical and electrical stimulation or only electrical stimulation. The hearing system, the binaural hearing system or the bimodal hearing system may further include one or more auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of a remote control, a remote microphone, an audio gateway device, a wireless communication device, e.g. a mobile phone (such as a smartphone) or a tablet or another device, e.g. comprising a graphical interface, a public-address system, a car audio system or a music player, or a combination thereof. The audio gateway may be adapted to receive a multitude of audio signals such as from an entertainment device like a TV or a music player, a telephone apparatus like a mobile telephone or a computer, e.g. a PC. The auxiliary device may further be adapted to (e.g. allow a user to) select and/or combine an appropriate one of the received audio signals (or combination of signals) for transmission to the at least one hearing device. The remote control is adapted to control functionality and/or operation of the at least one hearing device. The function of the remote control may be implemented in a smartphone or other (e.g. portable) electronic device, the smartphone/electronic device possibly running an application (APP) that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to (relatively) enhance a target acoustic source among a multitude of acoustic sources in the user's environment and/or to attenuate other sources (e.g. noise). In one aspect, the directional system is adapted to detect (such as adaptively detect) from which direction a particular part of the microphone signal originates. This may be achieved by using conventionally known methods. The signal processing unit may include an amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal to the ear of the user, a mechanical stimulation applied transcutaneously or percutaneously to the skull bone, an electrical stimulation applied to auditory nerve fibers of a cochlea of the user. In some hearing devices, the output unit may include one or more output electrodes for providing the electrical stimulations such as in a Cochlear Implant, or the output unit may include one or more vibrators for providing the mechanical stimulation to the skull bone.

A Cochlear Implant typically includes i) an external part for picking up and processing sound from the environment, and for determining sequences of pulses for stimulation of the electrodes in dependence on the sound from the environment, ii) a (typically wireless, e.g. inductive) transcutaneous communication link for transmitting information about the stimulation sequences and/or for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing device comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

FIG. 1 illustrates a multi-layer electrode lead 100, e.g. comprised by a cochlear hearing aid system (not shown). Electrode lead 100 comprises an electrode carrier 110, a chemical gelatin layer 120 (an example of the first layer) and a physical gelatin layer 130 (an example of the second layer). Chemical gelatin layer 120a, 120b, 120c may consist of one or more sub-layers, e.g. two, three or N sub-layers, and/or have different thicknesses, e.g. a thickness of 2.5 μm (e.g. for one sub-layer), 5 μm (e.g. for two sub-layers) or N*2.5 μm (e.g. for N sub-layers), with N being an arbitrary positive integer. In this way, a desired final thickness of the coating can be achieved. In a step 1, the electrode carrier 110 coated with the chemical gelatin layer 120a, 120b, 120c is additionally coated with the physical gelatin layer 130 which is disposed on and encloses the chemical gelatin layer 120. Such a double-layer coating of electrode carrier 110 is particularly advantageous for controlling an amount of drug released from the first layer 120. Further, chemical gelatin layer 120 offers a strong attachment of the gelatin coating on a silicone surface of the electrode carrier 110 by providing covalent (or ionic) bonding. A "base" thickness of 2.5 μm is advantageous in that such a thickness may typically be well-controlled when coating the electrode carrier 110. The second layer (physical gelatin layer 130) offers high lubricity, thereby reducing a possible cochlear trauma when inserting electrode lead 100 into a recipient's cochlea.

Figure 2:
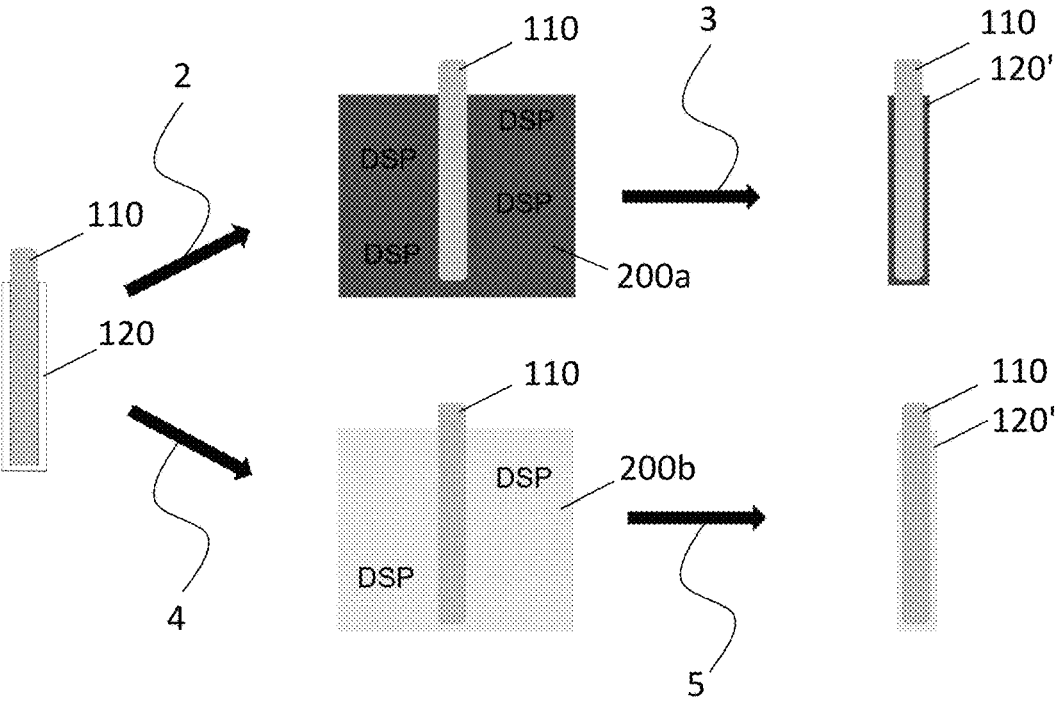
FIG. 2 schematically illustrates applying a drug solution to a gelatin coated electrode carrier.

FIG. 2 illustrates applying a drug solution 200a, 200b (an example of the release drug solution) to a gelatin coated electrode carrier 110. Specifically, electrode carrier 110 is coated with a chemical gelatin layer 120. In steps 2, 4, the gelatin coated electrode carrier 110 is dipped into the drug solution 200a, 200b. Drug solution 200a, 200b is a solution, e.g. an aqueous solution, containing dexamethasone sodium phosphate (DSP). While drug solution 200a is a saturated solution with a concentration of 100 mg/ml, drug solution 200b has a concentration of 1 mg/ml. It is to be understood that any concentration in between these two values, such as 10 mg/ml, 20 mg/ml, 30 mg/ml, is also disclosed herewith. When dipped into the drug solution 200a, 200b, chemical gelatin layer 120 (i.e. the coating of electrode carrier 110) swells and the drug, i.e. DSP, is trapped in the chemical gelatin layer 120 (an example of the dexamethasone sodium phosphate being embedded in the first layer). On the other hand, DSP is also deposited on a surface of chemical gelatin layer 120 (a further example of the dexamethasone sodium phosphate being embedded in the first layer). After sufficiently swelling chemical gelatin layer 120, as indicated by steps 3, 5, the gelatin coated electrode carrier 110 is removed from the drug solution 200a, 200b. An amount of drug, i.e. DSP, potentially released from chemical gelatin layer 120' depends on the concentration of the drug solution 200a, 200b and amounts, e.g., to 175 μg in 70 μl of perilymph for the saturated drug solution 200a and to 3 μg in 70 μl of perilymph for drug solution 200b. In other words, an amount of drug loaded into/onto chemical gelatin layer 120 may advantageously be controlled by means of the concentration of the drug solution 200a, 200b.

Figure 3:
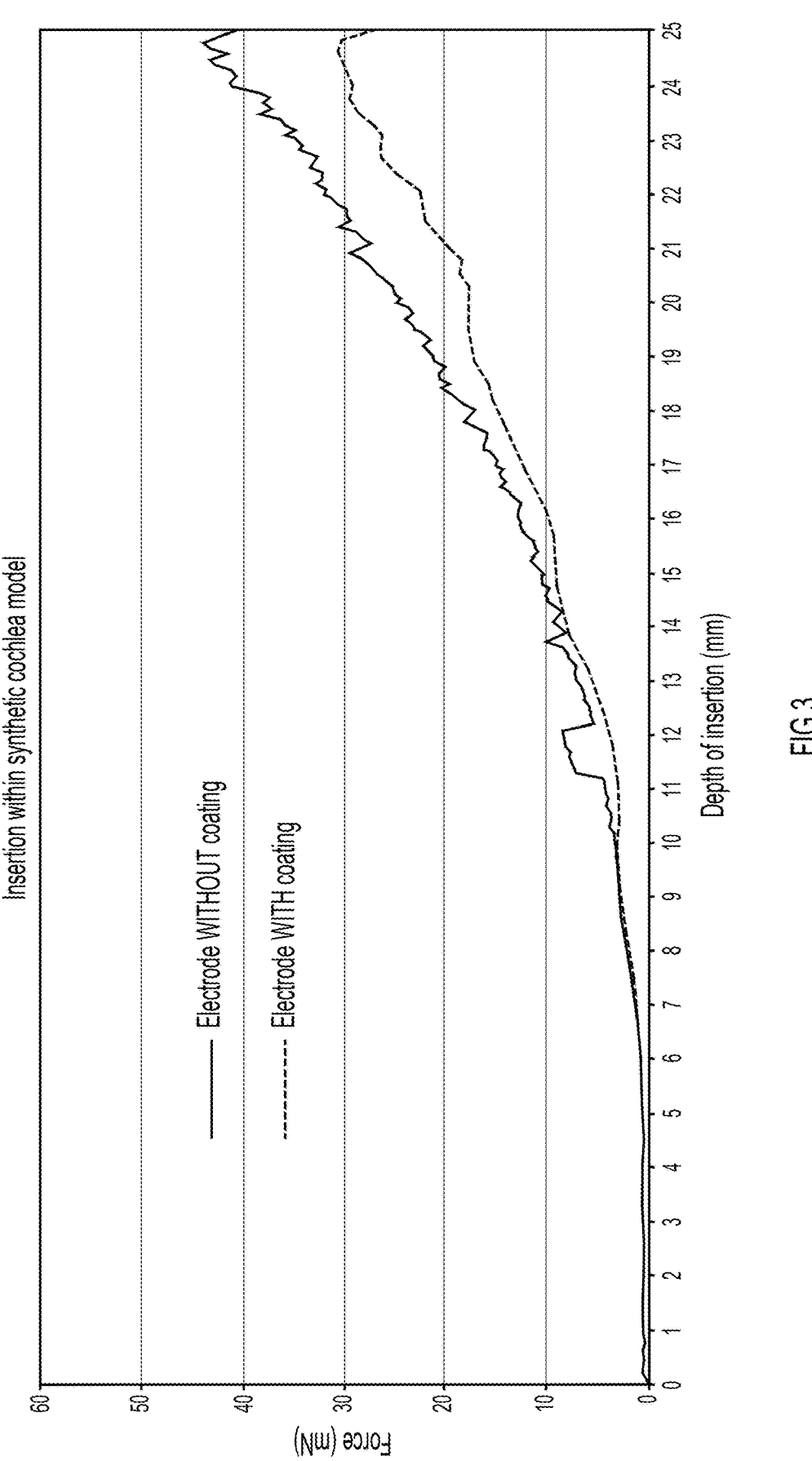
FIG. 3 shows an insertion force of an electrode lead when inserted into a synthetic cochlea as a function of a course standard.

FIG. 3 shows an insertion force of an electrode lead when inserted into a synthetic cochlea as a function of a course standard. Thereby, the insertion force induced by an electrode lead, e.g. an electrode array, without any coating is shown as the black line, and the insertion force induced by an electrode lead with a first chemical gel coating (an example of the first layer) and a second physical gel coating (an example of the second layer) is shown as the grey line. The course standard may be understood as a proxy of the depth of penetration, i.e. depth of insertion, of the electrode lead into the cochlea. As can be seen in FIG. 3, the final maximum insertion force is reduced by 30% such that a possible cochlear trauma when inserting the electrode lead into a recipient's cochlea is mitigated.

Figure 4A:
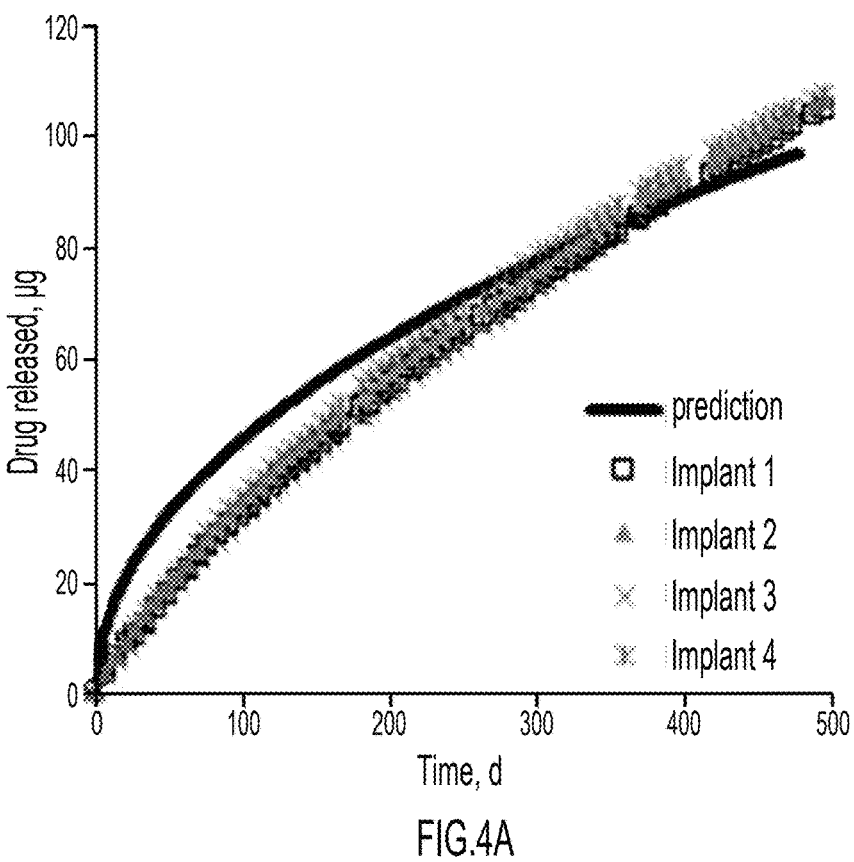
FIG. 4A schematically shows an amount of released drug as a function of time for a silicone electrode loaded with 10% dexamethasone.

FIG. 4A shows an amount of released drug (in μg) as a function of time (in days) for a silicone electrode loaded with 10% dexamethasone. To give some background, dexamethasone crystals may be mixed with silicone and when a device containing the silicone (e.g. the silicone electrode) gets in contact with body liquid, e.g. perilymph, the dexamethasone crystals dissolve and cause an anti-inflammatory effect on surrounding cells. As shown in FIG. 4A, an amount of drug, i.e. dexamethasone released as a function of time is approximately between 0 and 110 μg during a time period of between 0 and 500 days (an example of a long-term drug release). While the solid black line indicates a prediction of the released drug as a function of time, the squares, triangles, crosses and stars indicate different measurements.

Figure 4B:
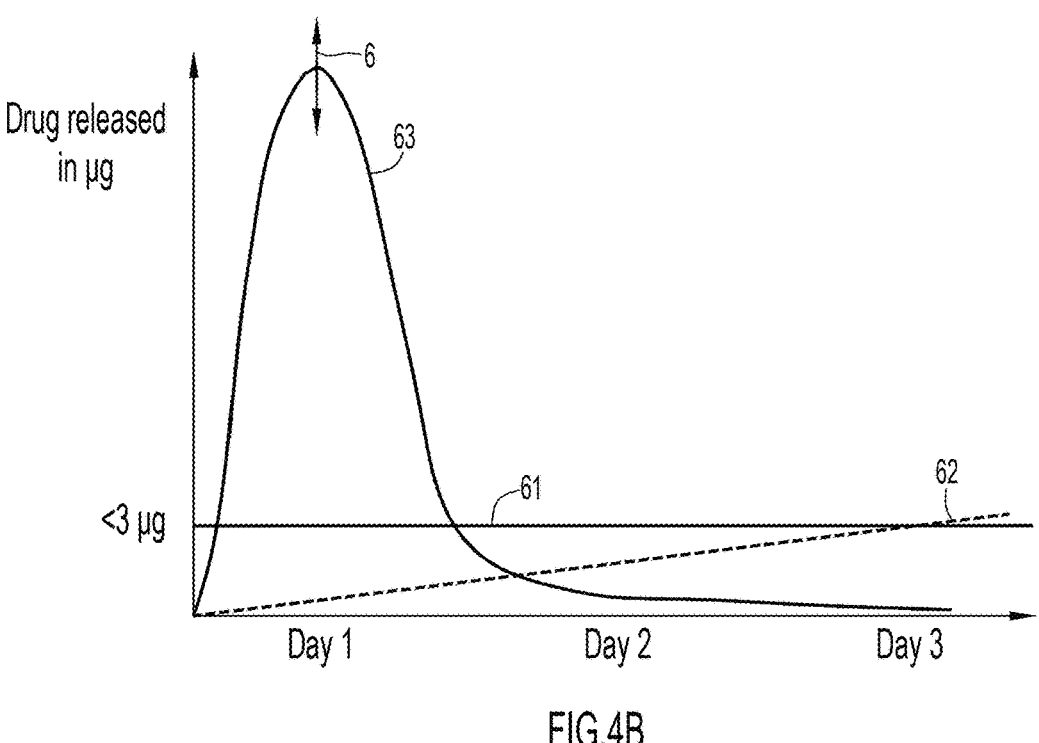
FIG. 4B schematically shows an amount of released drug as a function of time for a silicone electrode loaded with 10% dexamethasone and for a pure silicone electrode with a dexamethasone-loaded gelatin coating.

FIG. 4B shows an amount of released drug (in μg) as a function of time (in days) for a silicone electrode loaded with 10% dexamethasone and for a pure silicone electrode with a dexamethasone-loaded gel coating. Thereby, curve 61 indicates a threshold of 3 μg dexamethasone. As already described with reference to FIG. 4A, while the dexamethasone-loaded silicone electrode provides long-term drug release (cf. curve 62), a dexamethasone-loaded gel coating provides short-term drug release (cf. curve 63). Thus, FIG. 4B shows that a silicone electrode loaded with 10% dexamethasone (an example of the electrode carrier being made of silicone and being loaded by dexamethasone) and additionally coated with a dexamethasone-loaded gel coating (an example of a first layer in which dexamethasone sodium phosphate is embedded) allows to achieve a superposition of an increased or peak short-term drug release, e.g. over several hours, and a subsequent long-term drug release, e.g.

over several years. As indicated by arrow 6, a peak of the short-term drug release may be modulated.

Figure 5A:
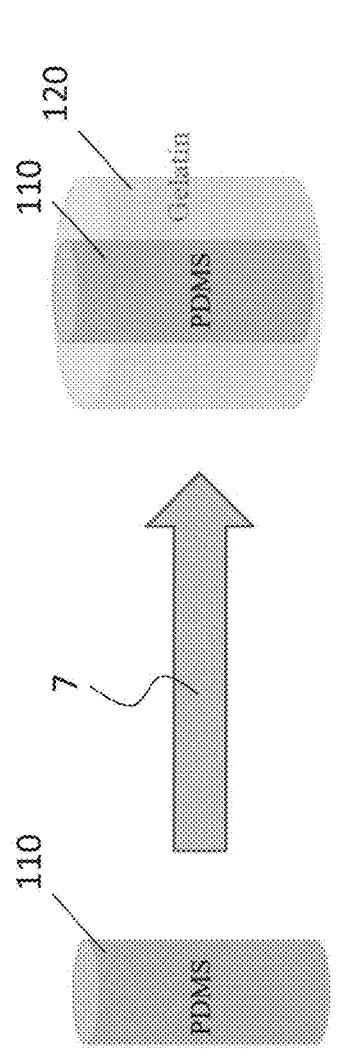
FIG. 5A schematically illustrates gelatin coating a PDMS fiber.

FIG. 5A illustrates gelatin coating (an example of applying a first layer) a PDMS (Polydimethylsiloxane) fiber 110 (an example of the electrode carrier) with a gelatin layer 120 (an example of the first layer), step 7.

Figure 5B:
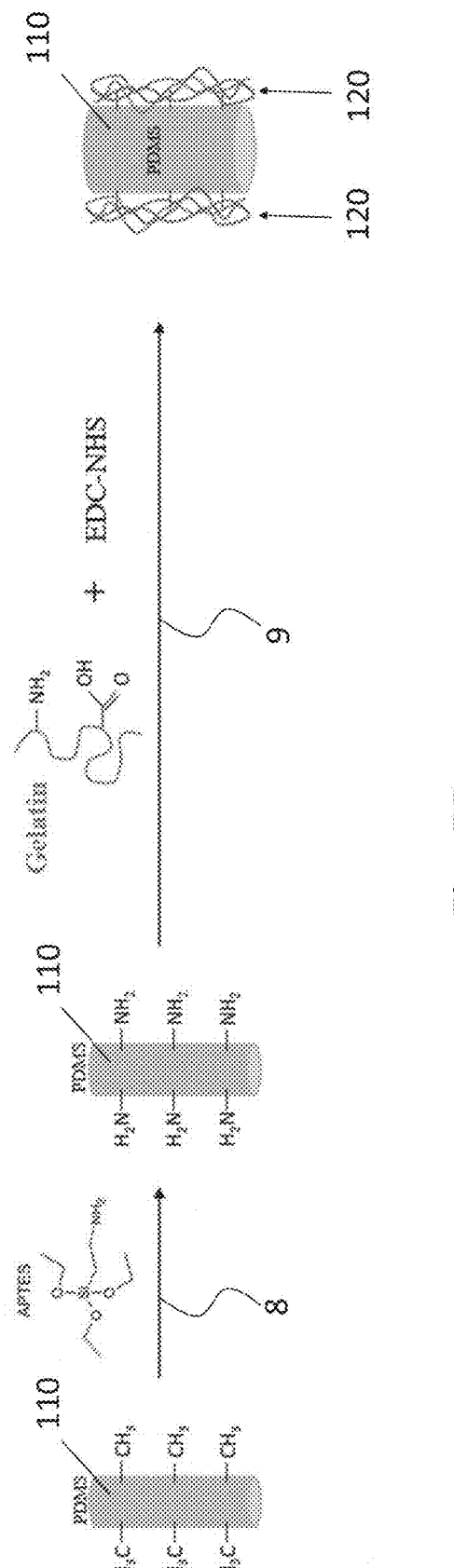
FIG. 5B schematically illustrates a first and a second step of gelatin coating a PDMS fiber.

FIG. 5B schematically illustrates a first step 8 and a second step 9 of gelatin coating the PDMS fiber 110. In the first step 8, the PDMS fiber 110 including a plurality of $CH_3$ groups undergoes silanization, i.e. is covered with APTES (3-Aminopropyl)triethoxysilane), thereafter including a plurality of $NH_2$ groups, as shown. In the second step 9, the PDMS fiber 110 including the plurality of $NH_2$ groups is then chemically cross-linked and grafted with gelatin and EDC-NHS (an example of the coupling agent). Thus, after steps 8 and 9, the PDMS fiber 110 is coated with a gelatin layer 120 including gelatin and EDC-NHS (an example of the first layer including both the gelatin substance and a coupling agent).

Figure 6:
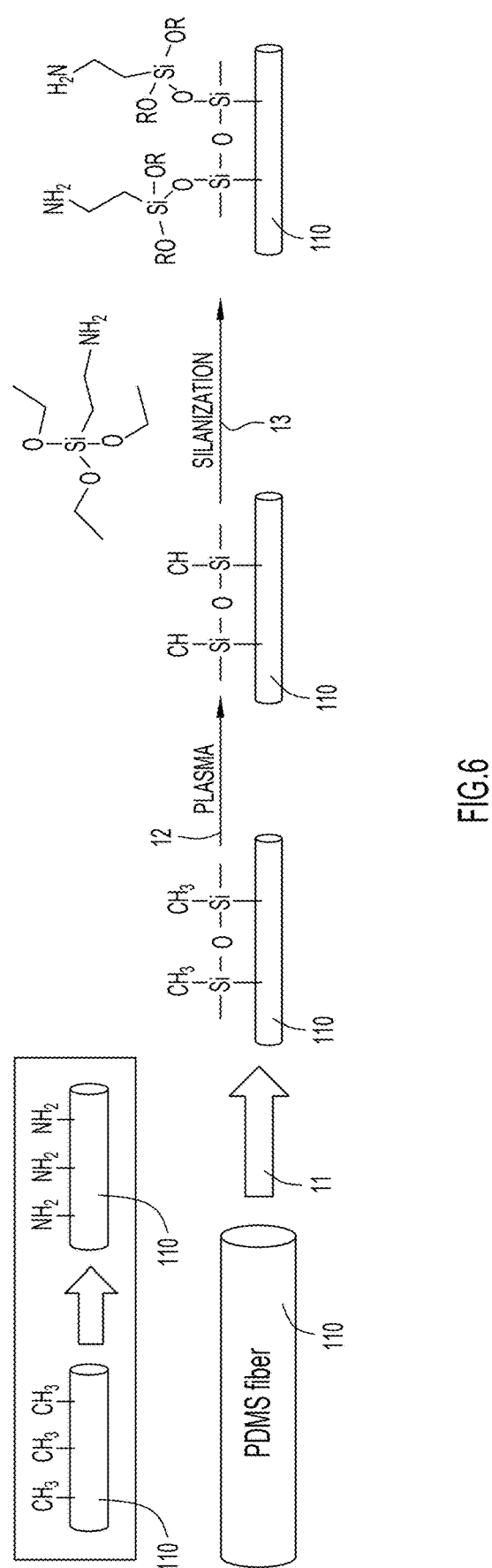
FIG. 6 schematically illustrates some sub-steps of the first step of gelatin coating a PDMS fiber.

FIG. 6 illustrates some sub-steps 11, 12, 13 of the first step 8 of gelatin coating the PDMS fiber 110. As indicated by sub-step 11, the PDMS fiber 110 includes a plurality of $CH_3$ groups. As indicated by sub-step 12, the PDMS fiber 110 then undergoes a low-pressure plasma-system treatment, thereafter including a plurality of OH groups instead of the $CH_3$ groups. Then, as indicated by sub-step 13, the actual silanization as described with reference to FIG. 5B is performed, e.g. in a reactor, after which the PDMS fiber 110 includes a plurality of $NH_2$ groups, as shown.

FIG. 7A shows a process 1000 comprising some sub-steps 1100, 1200, 1300, 1400, 1500, 1600 of the second step 9 of gelatin coating a PDMS fiber. FIGS. 7B and 7C show some details of some sub-steps of the second step of gelatin coating a PDMS fiber.

Sub-step 1100 comprises B(-type) gelatin solubilization at 55° C. overnight and EDC-NHS coupling agent addition, whereby an amount of EDC-NHS in the gelatin solution is approximately 20 mM (millimolar, i.e. 0.001 mol/l). Thereby, the coupling agent EDC-NHS is added for grafting and chemical cross-linking the gelatin with the PDMS fiber. In detail, as illustrated in FIG. 7B, a (B-)gelatin solution 300 having a gelatin concentration of, e.g. 10 wt %, and having a temperature of about 55° C. is provided in a jar 35. Then, as indicated by arrow 14, the coupling agent EDC-NHS is added to the gelatin solution 300 such that the gelatin-EDC-NHS solution 400 comprises both the gelatin and the EDC-NHS.

Sub-step 1200 comprises dip-coating the PDMS fiber (an example of dip-coating the electrode lead into a liquid). In detail, as illustrated in FIG. 7C, the PDMS fiber 110 is immersed into the solution 400 (an example of the liquid comprising the gelatin substance and a coupling agent), step 15, is left immersed in the solution 400 for a predetermined amount of time and is then withdrawn from the solution 400, step 16. After withdrawal, the PDMS fiber 110 is coated with a gelatin layer 120. Thereby, a speed of immersing the PDMS fiber 110 into the solution 400 may amount to about, in particular exactly, 10 mm/s and a speed of withdrawing the PDMS fiber 110 from the solution 400 may amount to about, in particular exactly, 5 mm/s. A time, for which the PDMS fiber 110 is left immersed in the solution 400 (i.e. a dwell time) is variable, e.g. in the range of seconds to minutes. A time, during which the PDMS fiber dries amounts to about, in particular exactly, 5 s.

After the dip-coating, the coated PDMS fiber 110 is heated at 37° C. during 3 hours, sub-step 1300 (an example for heating the electrode lead at a temperature between 30°

C. and 45° C.), washed with hot water having a temperature of about, in particular exactly, 55° C. in an ultra-sonic bath, sub-step 1400 (an example of cleaning the electrode lead with water having a temperature of between 45° C. and 65° C.), dried with liquid nitrogen, sub-step 1500 (an example of drying the electrode lead and cooling the electrode lead at below 0° C.), and stored in a Petri box in a fridge, sub-step 1600.

Figure 8A:
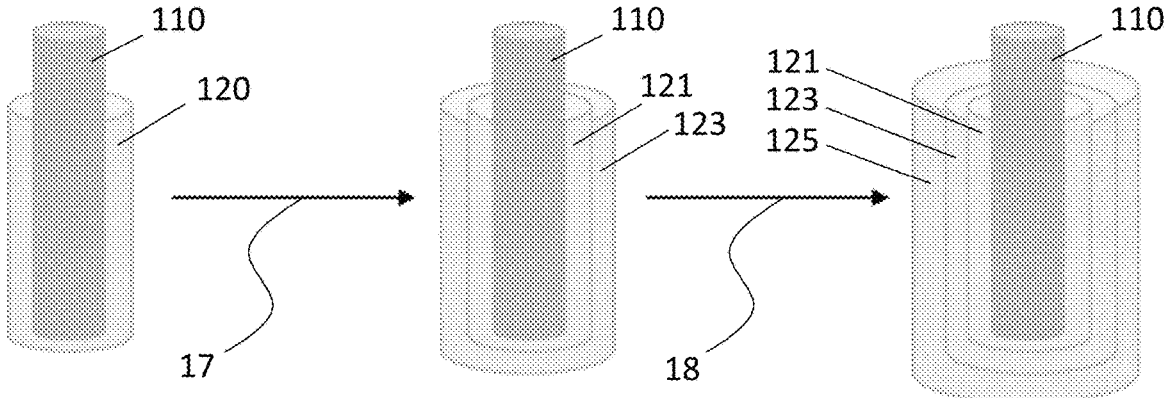
FIG. 8A schematically illustrates gelatin coating a PDMS fiber cycle by cycle.

FIG. 8A illustrates gelatin coating a PDMS fiber 110 cycle by cycle. In steps 17, 18, a PDMS fiber 110 already coated with a gelatin layer 120, 121, e.g. as described above, is coated with two further gelatin layers 123, 125, e.g. as described above. Such a coating cycle by cycle provides the advantage of an improved reproducibility and control of a thickness of the gelatin coating.

Figure 8B:
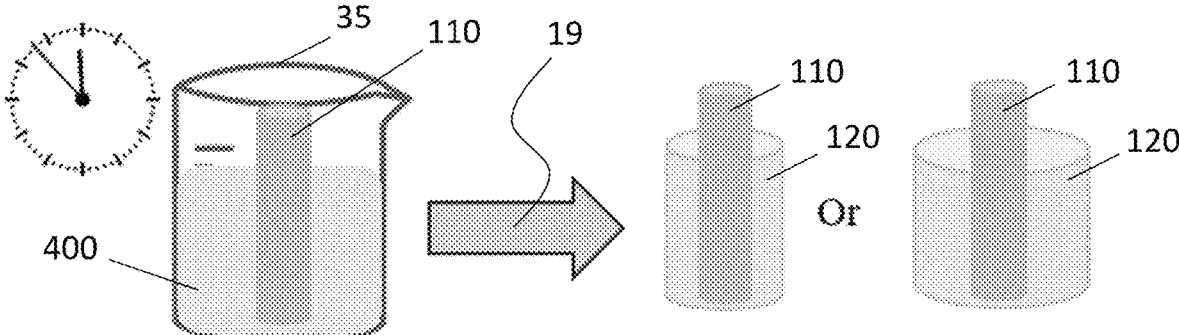
FIG. 8B schematically illustrates gelatin coating a PDMS fiber with one cycle and varying immersion time.

FIG. 8B illustrates gelatin coating a PDMS fiber 110 with one cycle and varying immersion time. In step 19, the PDMS fiber 110 is left in the jar 35 for a variable immersion time, thereby controlling a thickness of the resulting gelatin layer 120, as shown in the figure. Such a coating with only one cycle and a variable immersion time provides the advantage of a less complex coating process while still having high reproducibility and control of a thickness of the gelatin coating.

Both, coating cycle by cycle as well as coating with a variable immersion time have been tested for electrode leads comprising only silicone (embodiment 1), silicone with Pt (platinum) (embodiment 2), and for electrodes (embodiment 3).

For embodiment 1, i.e. for only-silicone fibers, a coating cycle by cycle has been performed and it has been found that for 1, 3, 4, and 10 cycles, respectively, a coating thickness of approximately 1.7 μm, 5-6 μm, 7 μm and 17 μm was achieved.

For embodiment 2, i.e. for silicone fibers with Pt, a coating with a variable immersion time of 10, 20, 30, 40, and 50 seconds, respectively, has been performed and it has been found that for an immersion (or dwell) time of 20 seconds at 60° C., a coating thickness of approximately 2.5 μm was achieved.

For embodiment 3, i.e. for electrodes (which are harder to cut), a coating with an immersion (or dwell) time of 20 seconds has been performed and it has been found that for an immersion (or dwell) time of 20 seconds at 60° C., a coating thickness of approximately 2.5 μm was achieved.

Figure 9:
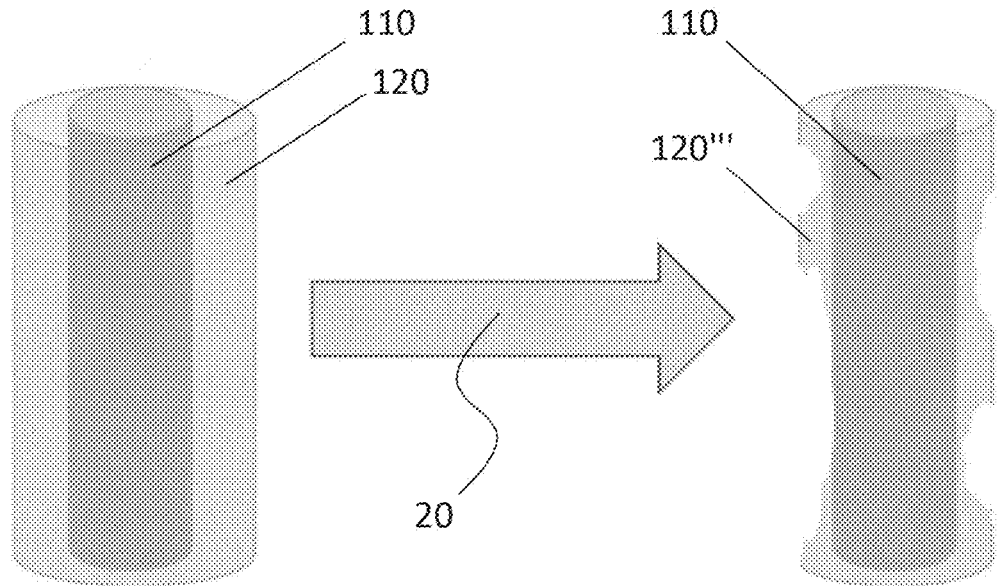
FIG. 9 schematically illustrates degradation of a gelatin coating.

FIG. 9 illustrates degradation of a gelatin coating 120, 120'''. In step 20, the gelatin coating is brought into contact with water having a temperature of 37° C., i.e. imitating water in human cells. As a result of getting into contact with the water, as shown, the gelatin coating 120, 120''' degrades. In particular, it has been found that after two days in PBS (phosphate-buffered saline) the gelatin is totally destroyed, while for immersion in homemade PBS, the swollen gel remains in the pillbox.

Figure 10:
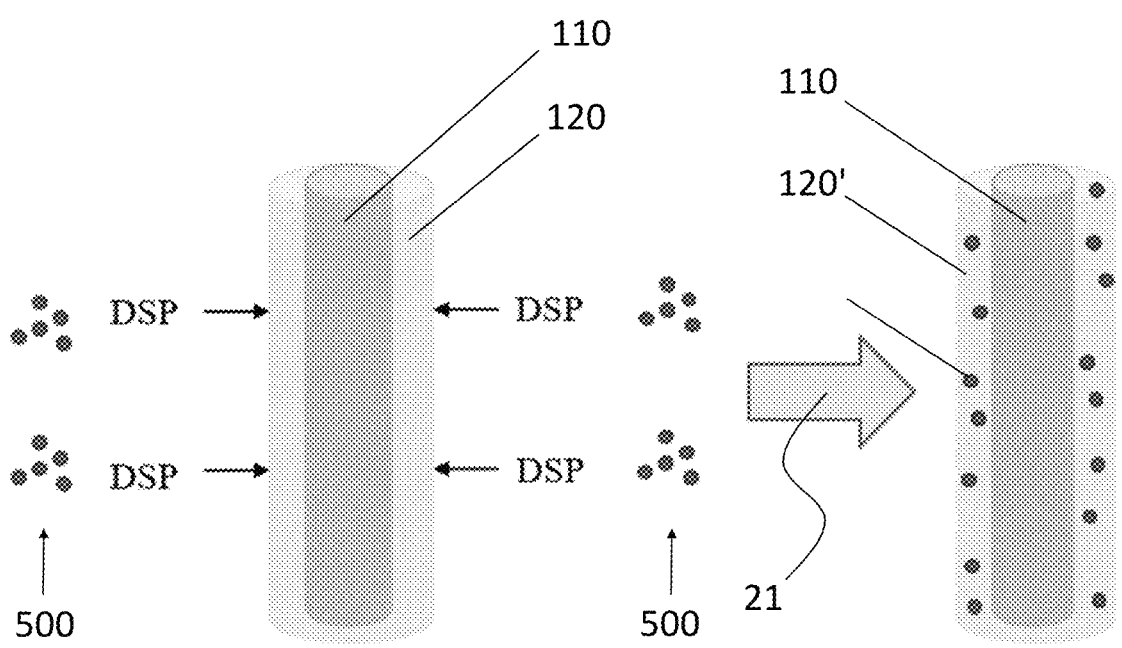
FIG. 10 schematically illustrates encapsulating dexamethasone sodium phosphate in a gelatin coating.

FIG. 10 illustrates encapsulating dexamethasone sodium phosphate (DSP) 500 in a gelatin coating 120 (an example of applying a release drug solution into or onto the first layer). As shown, in a step 21, the DSP 500 is embedded into, absorbed, resorbed, soaked up and/or sucked up by the gelatin coating 120 such that the gelatin coating 120' contains the DSP 500 after the step 21.

Figure 11:
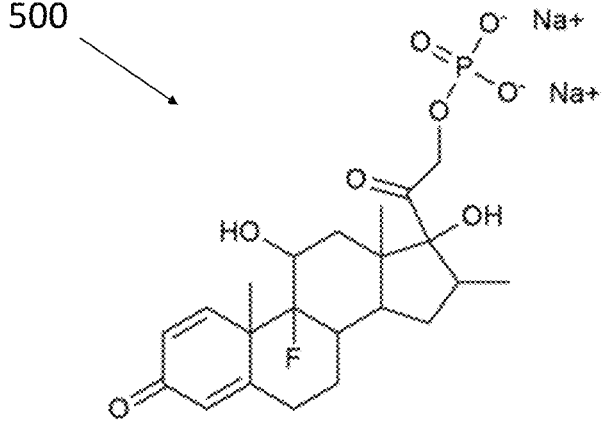
FIG. 11 schematically shows the structural formula of dexamethasone sodium phosphate.

FIG. 11 shows the structural formula of dexamethasone sodium phosphate 500, the water soluble version of dexamethasone.

Figure 12A:
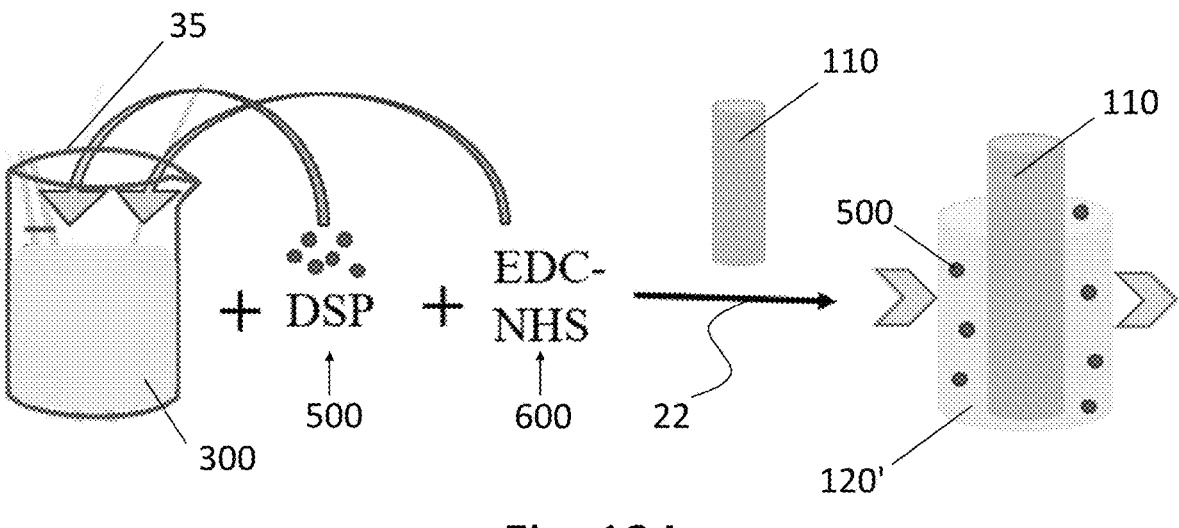
FIG. 12A schematically illustrates a first way of encapsulating dexamethasone sodium phosphate in a gelatin coating.

FIG. 12A illustrates a first way of encapsulating dexamethasone sodium phosphate 500 in a gelatin coating 120. First, the DSP 500 and the EDC-NHS coupling agent 600 are added to a gelatin solution 300, as shown in the figure (an example of the release drug solution being applied into the liquid). Then, in step 22, the PDMS fiber 110 is dip-coated (see description above for details of the dip-coating) into the gelatin solution including the DSP 500 and the EDC-NHS coupling agent 600 and then washed with cold water. As a result, the gelatin coating 120' contains the DSP 500. In other words, a first way of encapsulating the DSP 500 in a gelatin coating 120 comprises incorporation of the DSP 500 before the washing.

Figure 12B:
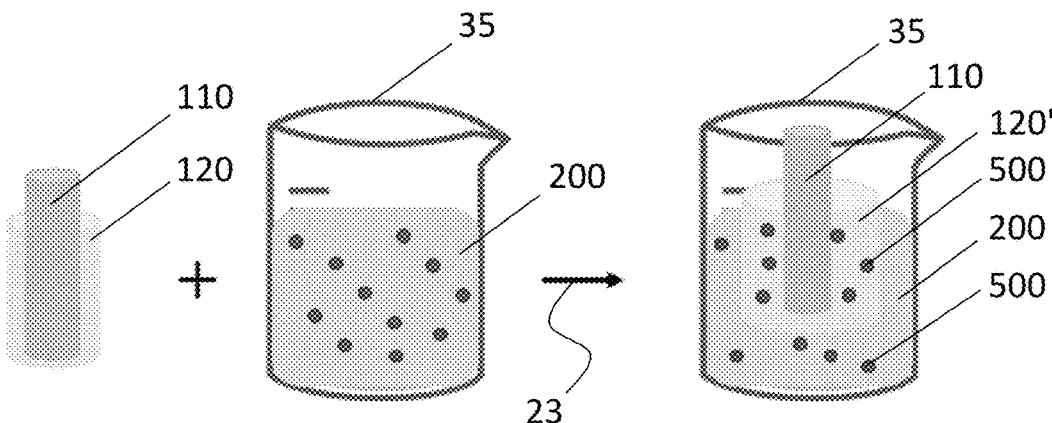
FIG. 12B schematically illustrates a second way of encapsulating dexamethasone sodium phosphate in a gelatin coating.

FIG. 12B illustrates a second way of encapsulating dexamethasone sodium phosphate 500 in a gelatin coating 120. Thereby, the already coated PDMS fiber 110 is immersed in an, e.g. aqueous, DSP solution 200 containing DSP 500 comprised by ajar 35, step 23 (an example of dip-coating the electrode lead with the first layer into a liquid comprising the release drug solution). The gelatin coating 120 swells and absorbs, resorbs, soaks up and/or sucks up the DSP 500 such that the swollen gelatin coating 120' contains the DSP 500. In other words, a second way of encapsulating the DSP 500 in a gelatin coating 120 comprises incorporation of the DSP 500 after the washing.

Swelling properties of gelatin have been tested for various conditions. In particular, the gelatin has been immersed in liquid nitrogen and the resulting swelling ratio has been measured. In the particular measurement, a swelling ratio (defined as a size of the swollen gelatin layer divided by a size of the dried gelatin layer) was found to amount to 1.63 without a treatment and to 1.62 with a liquid nitrogen treatment. Thus, in other words, treatment with liquid nitrogen appears to have no effect on the swelling ratio.

Figure 13:
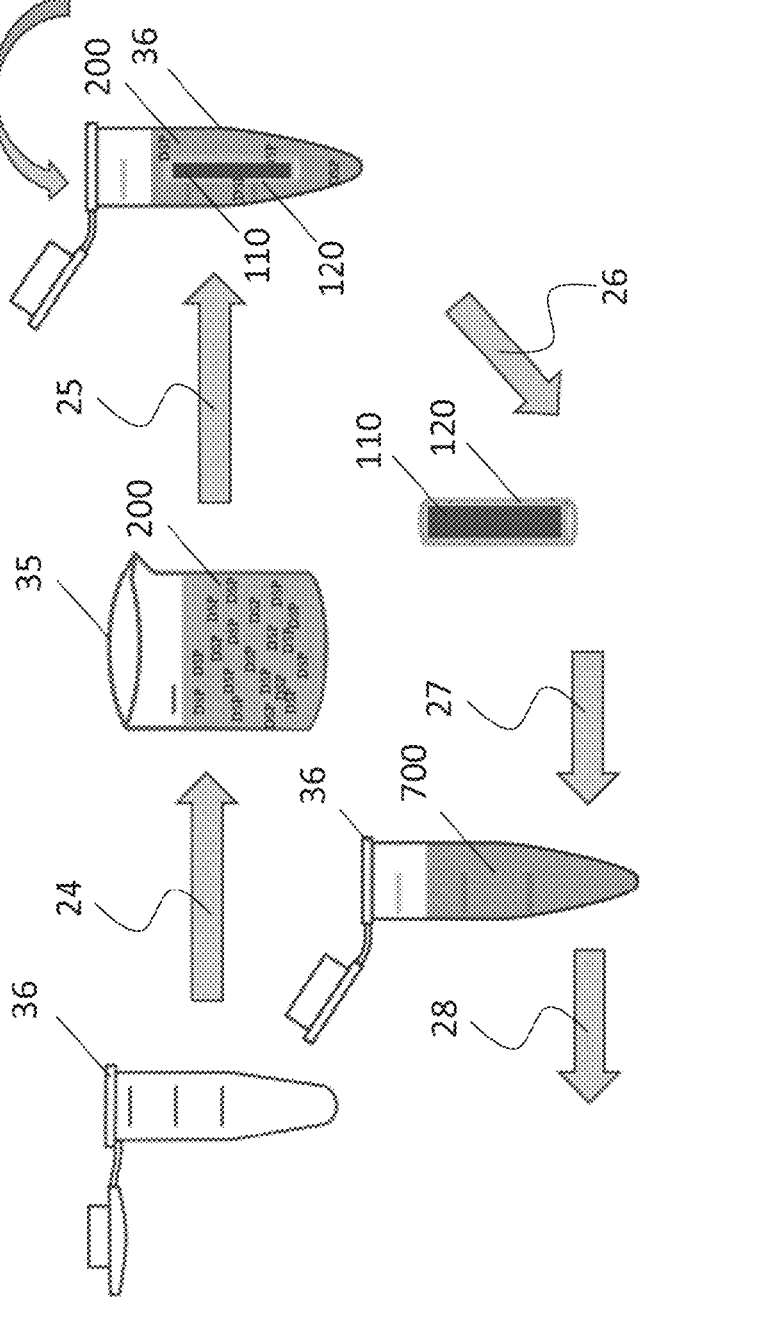
FIG. 13 schematically illustrates incorporation and release of dexamethasone sodium phosphate for a gelatin coated fiber.

FIG. 13 illustrates incorporation and release of dexamethasone sodium phosphate for a gelatin coated fiber. First, a 0.5 ml PCR tube 36 is filled with an, in particular aqueous, DSP solution 200, step 24. Then, a coated fiber 110 is immersed in the DSP solution 200 in pieces, step 25. The coated fiber 110 is left in the DSP solution 200 for swelling and DSP incorporation, whereby a swelling time amounts to about, in particular exactly, 1 hour and is calculated as $$\text{Swelling time} = \frac{H^2}{D} = \frac{\left(10^{-6}s\right)^2}{10^{-9}s - 10^{-12}s} = 10^{-3}s - 1s$$

After the swelling time, the coated fiber 110 is withdrawn from the DSP solution 200, step 26. The PCR tube 36 is filled with 200 µl of fresh water, step 27. Thereafter, the drug, i.e. DSP, is released by immersing the coated fiber 110 including the swollen gelatin coating 120 which in turn includes the DSP into the fresh water 700, step 28.

Figure 14:
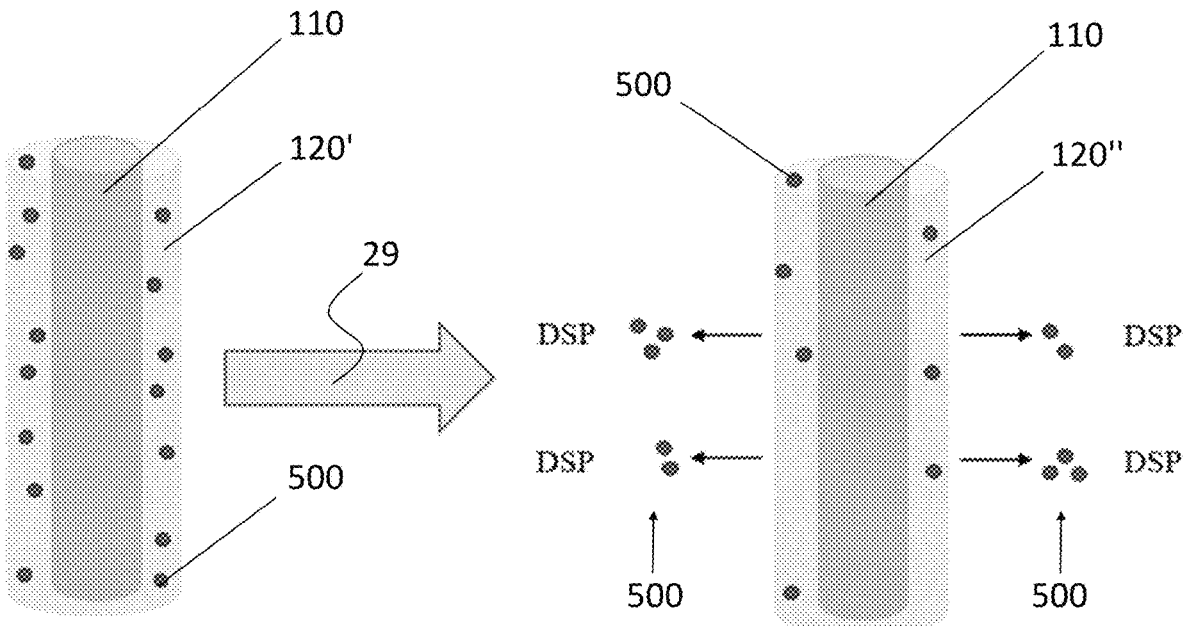
FIG. 14 schematically illustrates release of dexamethasone sodium phosphate from a gelatin coating.

FIG. 14 illustrates release of dexamethasone sodium phosphate 500 from a gelatin coating 120' coating a PDMS fiber 110. The coated fiber is immersed in water having a temperature of 37° C. in the dark, i.e. imitating water in human cells. The DSP 500 is released from the gelatin coating 120' into the water, step 29, leading to a reduced concentration of DSP 500 in the gelatin coating 120", as illustrated in the figure.

Figures 15A, 15B:
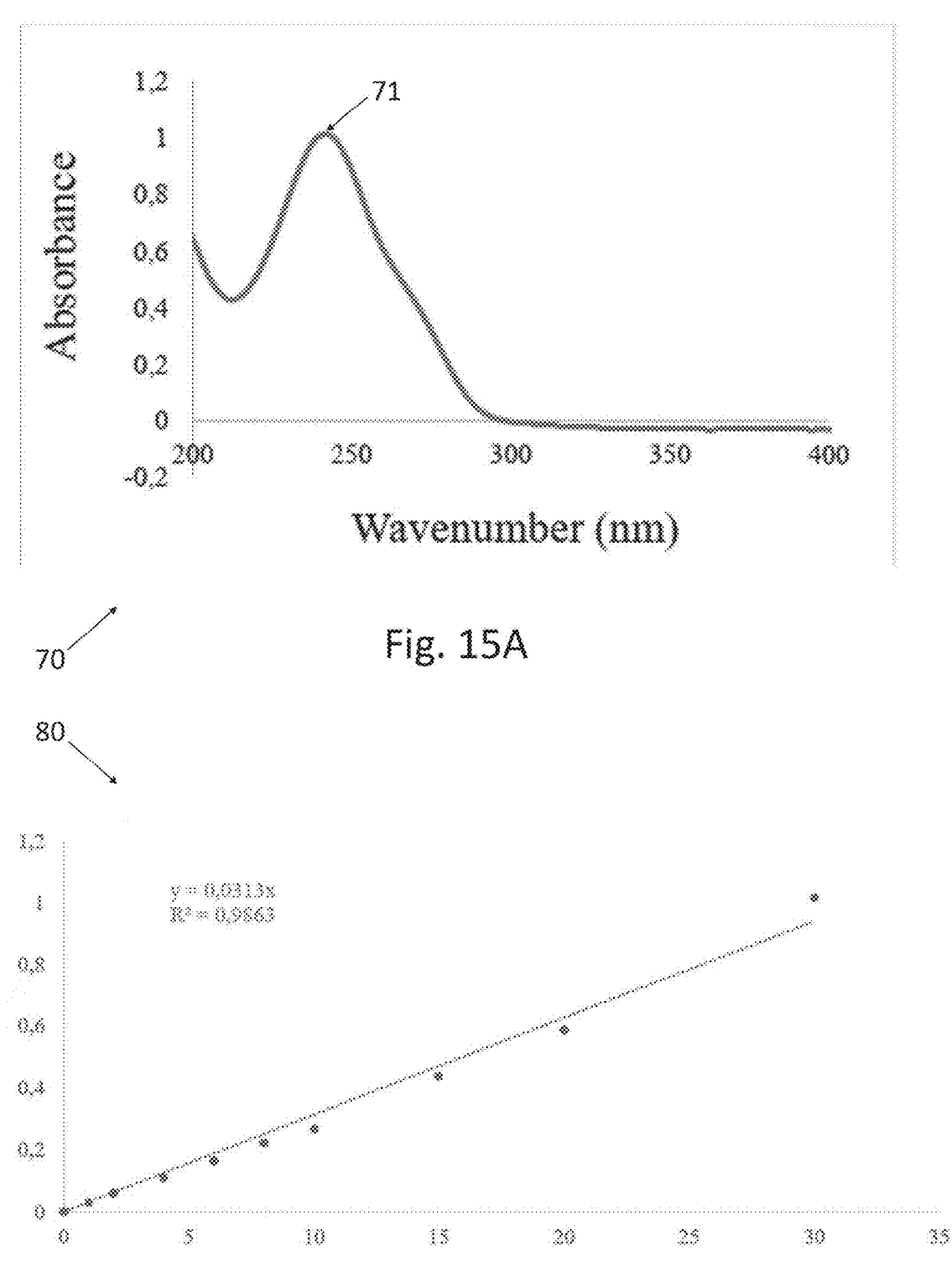
FIG. 15A schematically shows an absorbance curve of ultraviolet (UV) light as a function of the UV light wavelength.
FIG. 15B schematically shows a dexamethasone sodium phosphate calibration curve in ultraviolet (UV) visible spectroscopy at a wavelength of 242 nm.

FIG. 15A shows an absorbance curve of ultraviolet (UV) light for DSP as a function of the UV light wavelength. As illustrated, the absorbance reaches a local maximum 71 at a wavelength of 242 nm. Thus, in other words, an absorbance of UV light by DSP is maximum at a wavelength of 242 nm such that wavelength advantageously allows to determine a presence of DSP.

FIG. 15B schematically shows a dexamethasone sodium phosphate calibration curve in ultraviolet (UV) visible spectroscopy at a wavelength of 242 nm. As illustrated, the absorbance of UV light having a wavelength of 242 nm depends approximately linearly on the concentration of DSP (in µg/ml), whereby the absorbance (which amounts to between 0 and 1.2) may be approximated as 0.0313 times the concentration of DSP in µg/ml (which amounts to between 0 µg/ml and 30 µg/ml). Thus, UV spectroscopy at a wavelength of 242 nm advantageously allows to quantify the DSP concentration between 1 µg/ml and 30 µg/ml.

Figure 16:
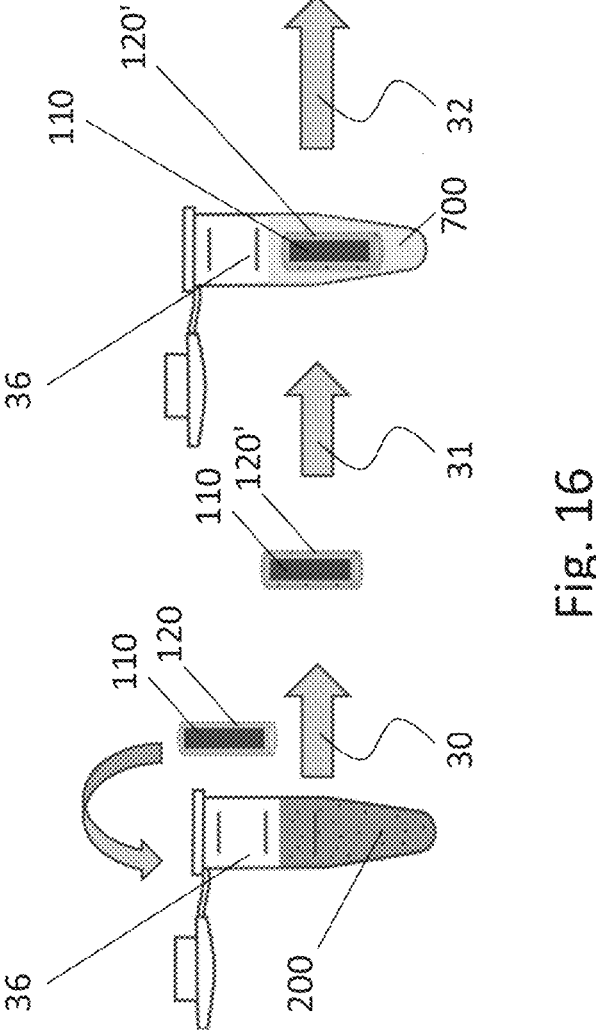
FIG. 16 schematically illustrates determining a release kinetic of a dexamethasone sodium phosphate-incorporated gelatin coating.

FIG. 16 illustrates determining a release kinetic of a dexamethasone sodium phosphate-incorporated gelatin coating. First, a 0.5 ml PCR tube 36 is filled with an, in particular aqueous, DSP solution 200 and a PDMS fiber 110 coated with a gelatin layer 120 is immersed in the DSP solution 200. After the swelling, the coated fiber is withdrawn from the DSP solution 200 and the gelatin layer 120' contains DSP, step 30. The PCR tube 36 is filled with 200 µl of fresh water and the PDMS fiber 110 coated with the gelatin layer 120 is immersed into fresh water 700, step 31. After about, in particular exactly, one day, the release of drug, i.e. of DSP, expected in the perilymph, is determined, step 32. The following relationship between the DSP concentration of the DSP solution 200 and the expected DSP concentration in the perilymph has been found:

| DSP solution concentration | DSP concentration in perilymph |
|---|---|
| more than 100 mg/ml (saturated) | $11 \times 10^3$ µg/ml (too high) |
| 1 mg/ml | 1.2 ± 0.3 µg/ml (nitrogen drying) (close to 5 µg/ml) |
| 1 mg/ml | 3.1 ± 0.1 µg/ml (air drying) (close to 5 µg/ml) |
| 1 mg/ml | 4.6 ± 0.9 µg/ml (no drying) (close to 5 µg/ml) |
| 0.1 mg/ml | 0 µg/ml (no release) |

As can be seen from the above table, by setting the concentration of DSP in the (mother) solution, the amount of drug loaded into the electrode coating can be set and/or controlled.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element, but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. An electrode lead, comprising:
an electrode carrier maintaining a plurality of electrode contacts and wires, wherein the electrode carrier is made of silicone and is loaded by dexamethasone;
a first layer of gelatin which is coated and chemically cross-linked selectively on a silicone outer surface of the electrode carrier, wherein dexamethasone sodium phosphate is embedded in the first layer; and
a second layer of gelatin which is coated and physically cross-linked onto the first layer.

2. The electrode lead of claim 1, wherein the first layer comprises a plurality of layers of gelatin that are coated and cross-linked in order to form the first layer.

3. The electrode lead of claim 1, wherein the first layer has a thickness of between 200 nm and 5 μm and/or is composed of a single layer or multiple layers.

4. The electrode lead of claim 1, wherein at least one of the first layer or the second layer includes a release drug solution.

5. The electrode lead of claim 4, wherein the release drug solution includes Dexamethasone Sodium Phosphate having a concentration of between 0.1 mg/mL and 100 mg/mL (saturated solution).

6. The electrode lead of claim 5, wherein a released Dexamethasone Sodium Phosphate concentration is between 0.1 and 175 μg in 70 μL of artificial perilymph.

7. The electrode lead of claim 4, wherein the release drug solution is configured to release a drug in a chosen duration of between 10 minutes and 1 day, depending on coating characteristics, in particular concentration, thickness and cross-linking.

8. The electrode lead of claim 1, wherein the first layer includes both a gelatin substance and a coupling agent.

9. The electrode lead of claim 8, wherein the gelatin substance of the first layer is coupled to stem cells targeting hair cells or neurons.

10. The electrode lead of claim 1, wherein a gelatin substance of the first layer is coupled to a Nerve Growth Factor (NGF).

11. An electrode lead, comprising:
an electrode carrier comprising a plurality of electrode contacts and wires, wherein the electrode carrier is loaded by dexamethasone;
a first layer of gelatin chemically cross-linked to a surface of the electrode carrier, wherein dexamethasone sodium phosphate is embedded in the first layer of gelatin; and
a second layer of gelatin physically cross-linked to the first layer of gelatin.

12. The electrode lead of claim 11, wherein the gelatin of at least one of the first layer of gelatin or the second layer of gelatin comprises B-type gelatin.

13. The electrode lead of claim 11, wherein the first layer of gelatin comprises a thickness of approximately 2.5 μm.

* * * * *